United States Patent
Lee

(10) Patent No.: US 11,622,989 B2
(45) Date of Patent: Apr. 11, 2023

(54) METHOD FOR INHIBITING MELANOMA CELL METASTASIS

(71) Applicant: ST. LOTUS BIOTECH CORP., Taichung (TW)

(72) Inventor: Chih-Chen Lee, Nantou County (TW)

(73) Assignee: ST. LOTUS BIOTECH CORP., Taichung (TW)

( * ) Notice: Subject to any disclaimer, the term of this patent is extended or adjusted under 35 U.S.C. 154(b) by 98 days.

(21) Appl. No.: 17/192,854

(22) Filed: Mar. 4, 2021

(65) Prior Publication Data

US 2021/0205402 A1 Jul. 8, 2021

Related U.S. Application Data

(62) Division of application No. 16/443,883, filed on Jun. 18, 2019, now abandoned.

(51) Int. Cl.

| | | |
|---|---|---|
| *A61K 36/9068* | (2006.01) | |
| *A61K 36/8967* | (2006.01) | |
| *A61K 36/78* | (2006.01) | |
| *A61K 36/888* | (2006.01) | |
| *A61K 36/725* | (2006.01) | |
| *A61K 36/23* | (2006.01) | |
| *A61K 36/185* | (2006.01) | |
| *A61K 36/53* | (2006.01) | |
| *A61K 36/77* | (2006.01) | |
| *A61K 9/00* | (2006.01) | |
| *A61P 35/04* | (2006.01) | |
| *A61K 36/481* | (2006.01) | |

(52) U.S. Cl.
CPC ........ *A61K 36/9068* (2013.01); *A61K 9/0053* (2013.01); *A61K 36/185* (2013.01); *A61K 36/23* (2013.01); *A61K 36/481* (2013.01); *A61K 36/53* (2013.01); *A61K 36/725* (2013.01); *A61K 36/77* (2013.01); *A61K 36/78* (2013.01); *A61K 36/888* (2013.01); *A61K 36/8967* (2013.01); *A61P 35/04* (2018.01); *A61K 2236/333* (2013.01)

(58) Field of Classification Search
None
See application file for complete search history.

(56) References Cited

FOREIGN PATENT DOCUMENTS

CN 106511915 * 3/2017

OTHER PUBLICATIONS

Kang, S. et al. Evaluation of Oriental Medicinal Herbs for Estrogenic and Antiproliferative Activities. Phytotherapy Research 20(11) 1017-9 Nov. 2006. (Year: 2006).*
Hsan K. et al. Current Research and Development of Chemotherapeutic Agents for Melanoma. Cancers 2:397-419 2010. (Year: 2010).*
Weng, C. et al. Anti-Invasion Effects of 6-Shogaol and 6-Gingerol . . . Molecular Nutrition & Food Research 54(11)1618-1627 Nov. 2010. (Year: 2010).*

* cited by examiner

*Primary Examiner* — Ralph J Gitomer
(74) *Attorney, Agent, or Firm* — Hannah Tien

(57) ABSTRACT

The present invention relates to a Chinese herbal medicine composition which is prepared from a raw material comprising the following ratio: 1 part by weight of *Lilium brownii* var. *viridulum*, 5 parts by weight of *Houttuynia cordata*, 2 parts by weight of *Atractylodes macrocephala*, 2 parts by weight of *Poria cocos*(Schw.) Wolf., 1 part by weight of *Ziziphi Spinosae* Semen, 3 parts by weight of *Adenophora morrisonensis*, 2 parts by weight of Semen *Astragali Complanati*, 0.5 parts by weight of *Zingiber officinale*, 5 parts by weight of *Tribulus terrestris*, 3 parts by weight of *Pogostemon cablin*, 0.5 parts by weight of *Ziziphus jujuba*, and 0.1 parts by weight of *Dimocarpus longan*. The invention also relates to a method of using the herbal composition for inhibiting melanoma cell metastasis. The invention also relates to a process for the preparation of the herbal composition.

5 Claims, 3 Drawing Sheets

Figure 1
Figure 1(A)
Figure 1 (B)
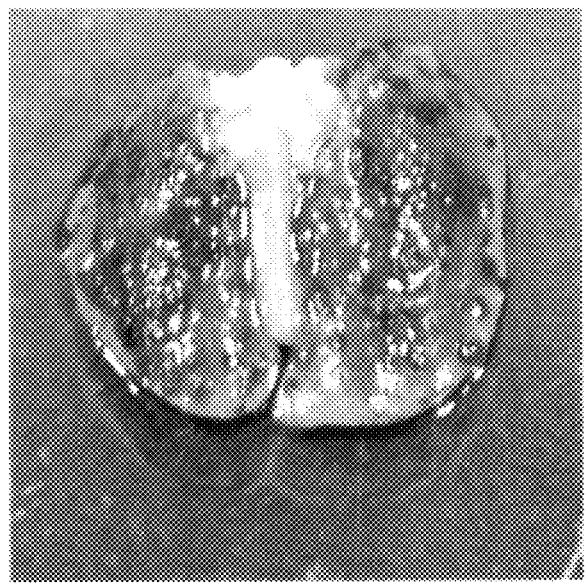

Figure 2(A)                                    Figure 2(B)

Figure 3
Figure 3(A)
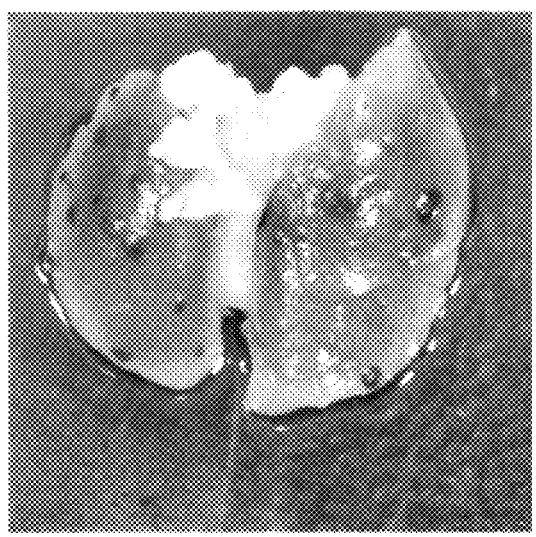
Figure 3(B)
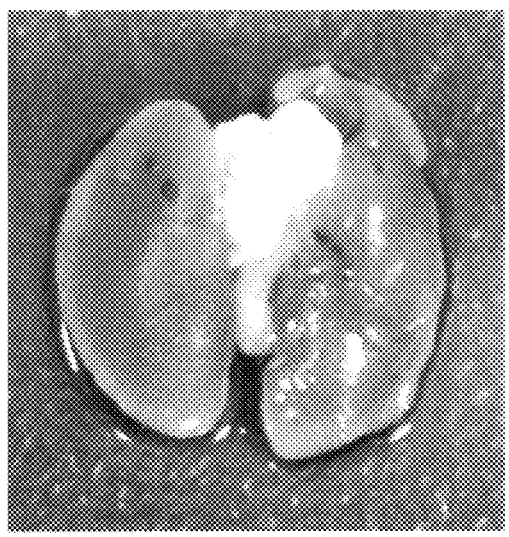

METHOD FOR INHIBITING MELANOMA CELL METASTASIS

CROSS-REFERENCES TO RELATED APPLICATIONS

This application is a divisional of the pending U.S. patent application Ser. No. 16/443,883 filed on Jun. 18, 2019, for which priority is claimed and is incorporated herein by reference in its entirety.

TECHNICAL FIELD

The present invention relates to a Chinese herbal medicine composition, which is used in a method for inhibiting melanoma cell metastasis and a method for preparing the same.

BACKGROUND OF THE INVENTION

Tumor metastasis is a complex process that usually involves several steps. First, the cancer cells detach from the primary site of a tumor, and migrate to the lymphatic system or blood vessels to destroy the vascular basement membrane and enter the lymph or blood. At this time, the cancer cells must escape from the attack of the immune system in order to survive, and adsorb to distant vascular endothelium, extravasate to a new metastatic site, and then regenerate into a tumor.

Melanoma is highly metastatic, and lung is one of the main organs to which it metastasizes. Melanoma having metastatic activity is a more dangerous skin cancer, it is also the main cause of death of skin cancers, about 75%, the prognosis is not good, and the rate for survival longer than 5 years is less than 5%.

DETAILED DESCRIPTION OF THE INVENTION

The present invention relates to a Chinese herbal medicine composition which is prepared from a raw material comprising the following ratio: 1 part by weight of *Lilium brownii* var. *viridulum*, 5 parts by weight of *Houttuynia cordata*, 2 parts by weight of *Atractylodes macrocephala*, 2 parts by weight of *Poria cocos*(Schw.) Wolf., 1 part by weight of *Ziziphi Spinosae* Semen, 3 parts by weight of *Adenophora morrisonensis*, 2 parts by weight of Semen *Astragali Complanati*, 0.5 parts by weight of *Zingiber officinale*, 5 parts by weight of *Tribulus terrestris*, 3 parts by weight of *Pogostemon cablin*, 0.5 parts by weight of *Ziziphus jujuba*, and 0.1 parts by weight of *Dimocarpus longan*.

In one embodiment, the *Tribulus terrestris* is *Tribulus taiwanese* belonging to the Zygophyllaceae family.

The present invention also relates to a method for inhibiting melanoma cells metastasis by administering to a subject in need thereof a reasonable dose of the Chinese herbal medicine composition to achieve the effect of inhibiting melanoma metastasis.

In one embodiment, the melanoma cells metastasis refers to metastasis of melanoma cells to lungs.

In one embodiment, the reasonable dose is from 1 to 5 grams of the Chinese herbal medicine composition per kilogram of body weight of the subject in need thereof.

In one embodiment, the Chinese herbal medicine composition is administered orally to the subject in need thereof.

In one embodiment, the herbal composition is administered to the subject in need thereof for 14 consecutive days.

The present invention also relates to a method for preparing a Chinese herbal medicine composition, which comprises the following steps of: soaking 5 parts by weight of *Tribulus terrestris* and 5 parts by weight of *Houttuynia cordata* in an organic solvent and filtering to form a filtrate; concentrating the filtrate into an extract; soaking 1 part by weight of *Lilium brownii* var. *viridulum*, 2 parts by weight of *Atractylodes macrocephala*, 2 parts by weight of *Poria cocos*(Schw.) Wolf., 1 part by weight of *Ziziphi Spinosae* Semen, 3 parts by weight of *Adenophora morrisonensis*, 2 parts by weight of Semen *Astragali Complanati*, 0.5 parts by weight of *Zingiber officinale*, 3 parts by weight of *Pogostemon cablin*, 0.5 part by weight of *Ziziphus jujuba* and 0.1 part by weight of *Dimocarpus longan* in water to obtain a soaking liquid; further concentrating the soaking liquid to obtain a concentrated liquid; mixing the extract and the concentrated liquid, subjecting to high temperature and high pressure, and concentrating to obtain the Chinese herbal medicine composition.

In one embodiment, the organic solvent is ethanol; in another embodiment, the concentration of the ethanol is 20%.

In one embodiment, the concentration of the filtrate is increased by 7 fold to obtain the extract.

In one embodiment, the concentration of the soaking liquid is increased by 10 fold to obtain the concentrated liquid.

BRIEF DESCRIPTION OF THE DRAWINGS

FIG. 1, FIG. 1(A) shows metastasis of melanoma cells to the lungs induced by $5\times10^4$ melanoma cells per mouse; FIG. 1(B) shows metastasis of melanoma cells to the lungs induced by $5\times10^4$ melanoma cells per mouse.

FIG. 2, FIG. 2(A) shows metastasis of melanoma cells induced by $7.5\times10^4$ melanoma cells per mouse; FIG. 2(B) shows the inhibitory effect of the orally administered Chinese herbal medicine composition of the present invention for 14 consecutive days (1 mg/kg body weight) on melanoma metastasis induced by $7.5\times10^4$ melanoma cells per mouse.

FIG. 3, FIG. 3(A) shows melanoma cells metastasis induced by $5\times10^4$ melanoma cells per mouse; FIG. 3(B) shows the inhibitory effect of the orally administered Chinese herbal medicine composition of the present invention for 14 consecutive days (1 mg/kg body weight) on melanoma metastasis induced by $5\times10^4$ melanoma cells per mouse.

EXAMPLES

Figure 2:
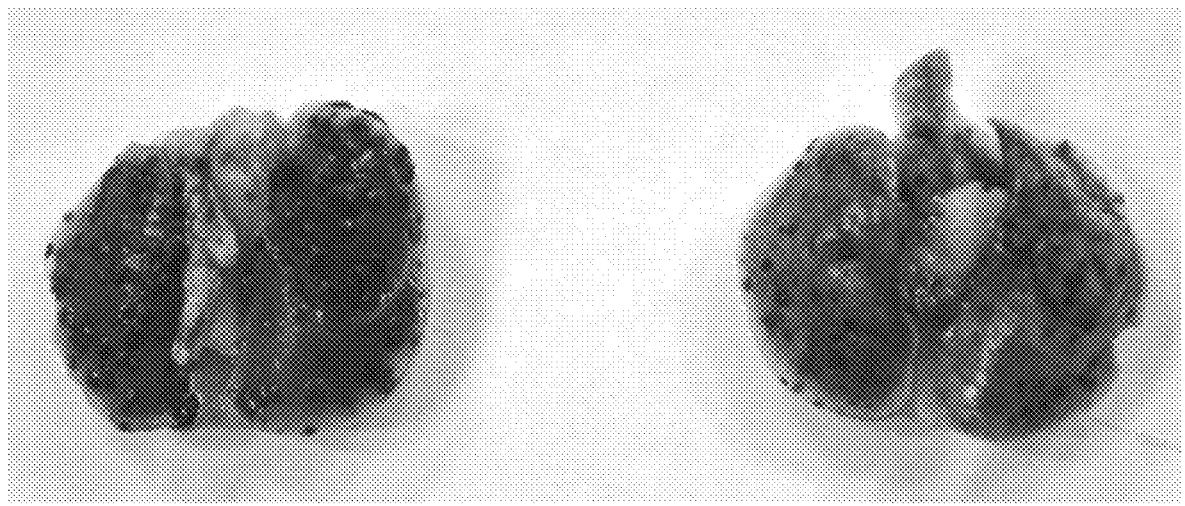

The following examples are not intended to be limiting, rather they merely present various aspects of the present invention.

Example 1. Method for Preparing the Chinese Herbal Medicine Composition of the Present Invention After 5 kg of *Tribulus taiwanense* and 5 kg of *Houttuynia cordata* were soaked with 20% edible alcohol for 48 hours, a filtrate was obtained with Silica based columns, and then concentrated at high temperature to increase the concentration by 7 fold to form an extract. Other ten herbs including 1 kg of *Lilium brownii* var. *viridulum*, 2 kg of *Atractylodes macrocephala*, 2 kg of *Poria cocos*(Schw.) Wolf., 1 kg of *Ziziphi Spinosae* Semen, 3 kg of *Adenophora morrisonensis*, 2 kg of Semen *Astragali Complanati*, 0.5 kg of *Zingiber officinale*, 3 kg of *Pogostemon cablin*, 0.5 kg of *Ziziphus jujuba*, and 0.1 kg of *Dimocarpus longan* were washed and then soaked in drinking water for 24 hours, then concentrated at high temperature by 10 fold to obtain a concentrated liquid. After the extract and the concentrated liquid were mixed, then subjected to high temperature and high pressure (130° C., 2 atmospheres) for 3 hours in a sealed space to further concentrate by 5 fold.

Example 2, Animal Experiment of Melanoma Cell Metastasis Inhibition by the Chinese Herbal Medicine Composition of the Present Invention Laboratory Animals C57BL/6 mice were purchased from the Laboratory Animal Center of the BioLASCO Taiwan Co., Ltd., raised and treated according to the Guide for Care and Use of Laboratory Animals (NIH, 1985). The animals were brought into a nursing room for adaption for 2-3 weeks, weighing and clinical diagnosis were performed to screen out animals without any diseases, then those animals with similar body weight were selected (average value of the margin of error was 20%), they were divided into appropriate weight groups according to their body weight, and then the animals were randomly divided into different groups, 6 animals in each group, a total of 4 groups. The distribution of each group is shown in Table 1.

TABLE 1

Doses of the Chinese herbal medicine composition and animal distribution in the present invention

| Group | Dose (g/Kg body weight) | Number of mice |
|---|---|---|
| 1 | Control group (0) | 6 |
| 2 | Low (1) | 6 |
| 3 | Medium (3) | 6 |
| 4 | High (5) | 6 |

Animal Experimental Model for Inducing Lung Carcinoma

In this animal experiment, $5 \times 10^4$ melanoma cells (B16-F10) were administered into the blood from the tail vein of the mice (C56BL/6; 6-7 weeks of age), the animals were divided into a control group (only melanoma cells were administered, no medicine was given), and three different groups fed with a low, a medium, and a high dose of the Chinese herbal medicine composition of the present invention (see Table 1), a total of 4 groups, lung carcinoma was evaluated after 14 days, the mice were sacrificed mainly by breaking their necks, their lungs were removed and immersed in 10% formaldehyde, melanoma cell colonies were evaluated by naked eyes and microscopes. The experiment was carried out according to the above-described groups, the number of samples in each group was 6.

$5 \times 10^4$ or $7.5 \times 10^4$ melanoma cells/mouse was administered into each mouse, after 14 days, it was found that $7.5 \times 10^4$ melanoma cells per mouse was enough to meaningfully induce metastasis of melanoma to the lungs (FIG. 1).

Example 3. Effect of the Chinese Herbal Medicine Composition of the Present Invention on Inhibiting Melanoma Cell Metastasis The metastasis of melanoma to the lungs was induced by administering $7.5 \times 10^4$ melanoma cells per mouse, and then the Chinese herbal medicine composition of the present invention was administered to the mice at an oral dose of 5 g/kg body weight, all mice were found dead the next day.

The metastasis of melanoma to the lungs was induced by administering a dose of $7.5 \times 10^4$ melanoma cells per mouse, and then the Chinese herbal medicine composition of the present invention was administered to the mice at an oral dose of 1 g/kg body weight for 14 consecutive days, the effect of inhibition of melanoma metastasis was observed (FIG. 2).

The metastasis of melanoma to the lungs was induced by administering a dose of $5 \times 10^4$ melanoma cells per mouse, and the Chinese herbal medicine composition of the present invention was administered into the mice at an oral dose of 1 gram per kilogram of body weight for 14 consecutive days, the effect of inhibition of melanoma metastasis was observed (FIG. 3).

Example 4. Method for Administering the Chinese Herbal Medicine Composition of the Present Invention for Inhibiting Melanoma Cell Metastasis and Dosage Limits Medium and high doses were respectively administered orally into three healthy mice, and all mice were found dead the next day (Table 2), the results indicated that the Chinese herbal medicine composition of the present invention might be toxic at higher doses.

TABLE 2

Doses of the Chinese herbal medicine composition and distribution of dead animals in the present invention

| Dose (g/Kg body weight) | Number of mice (died) |
|---|---|
| Medium (3) | 3 |
| High (5) | 3 |

The present invention has been described and illustrated in sufficient detail for one of ordinary skill in the art to which the present invention pertains to understand the method for preparing and utilizing the technique, however, varying substitutions, modifications, and improvements should be considered to be no different from the spirit and scope of the present invention.

One of ordinary skill in the art to which the present invention pertains can readily appreciate the objects of the present invention and obtain the ends and advantages as mentioned. The cells, animals, and processes and methods for producing the same are representative of the preferred embodiments and exemplary in nature, they are not intended to limit the scope of the present invention. The used cells, animals and processes, methods for producing the same are representative of preferred embodiments, are exemplary, and are not intended as limitations on the scope of the invention. Modifications therein and other uses that may occur to those skilled in the art and in the art of making or using the art are encompassed within the spirit of the present invention and are defined by the scope of the present invention.

What is claimed is:

1. A method for inhibiting melanoma cells metastasis by administering to a subject in need thereof an effective dose of a Chinese herbal medicine composition, which is to achieve an effect of inhibiting melanoma metastasis, wherein the Chinese herbal medicine composition is prepared from a raw material comprising the following ratio: 1 part by weight of *Lilium brownii* var. *viridulum*, 5 parts by weight of *Houttuynia cordata*, 2 parts by weight of *Atractylodes macrocephala*, 2 parts by weight of *Poria cocos* (Schw.) Wolf., 1 part by weight of *Ziziphi Spinosae* Semen, 3 parts by weight of *Adenophora morrisonensis*, 2 parts by weight of Semen *Astragali Complanati*, 0.5 parts by weight of *Zingiber officinale*, 5 parts by weight of *Tribulus terrestris*, 3 parts by weight of *Pogostemon cablin*, 0.5 parts by weight of *Ziziphus jujube*, and 0.1 parts by weight of dried *Dimocarpus longan*.

2. The method of claim 1, wherein the melanoma cells metastasis is metastasis to lungs.

3. The method of claim 1, wherein the effective dose is from 1 to 5 g of the Chinese herbal medicine composition per kg body weight of the subject in need thereof.

4. The method of claim 1, wherein the Chinese herbal medicine composition is administered orally to the subject in need thereof.

5. The method of claim 1, wherein the Chinese herbal medicine composition is administered to the subject in need thereof for 14 consecutive days.

\* \* \* \* \*